United States Patent
Hoernig

(10) Patent No.: US 10,751,007 B2
(45) Date of Patent: Aug. 25, 2020

(54) GENERATING AN IMAGE SEQUENCE

(71) Applicant: SIEMENS HEALTHCARE GMBH, Erlangen (DE)

(72) Inventor: Mathias Hoernig, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 6 days.

(21) Appl. No.: 15/636,942

(22) Filed: Jun. 29, 2017

(65) Prior Publication Data
US 2018/0000430 A1    Jan. 4, 2018

(30) Foreign Application Priority Data
Jun. 29, 2016 (DE) .......... 10 2016 211 766

(51) Int. Cl.
| | |
|---|---|
| G06K 9/00 | (2006.01) |
| A61B 6/02 | (2006.01) |
| A61B 6/00 | (2006.01) |
| A61B 6/03 | (2006.01) |
| G06T 7/00 | (2017.01) |
| A61B 6/04 | (2006.01) |

(52) U.S. Cl.
CPC .......... *A61B 6/022* (2013.01); *A61B 6/025* (2013.01); *A61B 6/03* (2013.01); *A61B 6/4241* (2013.01); *A61B 6/502* (2013.01); *G06T 7/0012* (2013.01); *G06T 7/0016* (2013.01); *A61B 6/0414* (2013.01)

(58) Field of Classification Search
None
See application file for complete search history.

(56) References Cited

U.S. PATENT DOCUMENTS

| | | | | |
|---|---|---|---|---|
| 5,671,157 | A * | 9/1997 | Saito | G06T 19/00 345/419 |
| 8,611,492 | B2 | 12/2013 | Jerebko | |
| 9,047,498 | B2 | 6/2015 | Dennerlein et al. | |
| 9,600,922 | B2 * | 3/2017 | Tsukagoshi | G06T 15/08 |
| 9,629,594 | B2 | 4/2017 | Hoernig | |
| 2003/0235265 | A1 * | 12/2003 | Clinthorne | A61B 6/14 378/4 |
| 2005/0084060 | A1 * | 4/2005 | Seppi | A61B 6/032 378/5 |
| 2005/0113681 | A1 * | 5/2005 | DeFreitas | A61B 6/502 600/426 |

(Continued)

FOREIGN PATENT DOCUMENTS

| | | |
|---|---|---|
| DE | 102011003135 A1 | 7/2012 |
| DE | 102011087337 A1 | 5/2013 |
| DE | 102012215997 A1 | 3/2014 |

*Primary Examiner* — Shervin K Nakhjavan
(74) *Attorney, Agent, or Firm* — Laurence Greenberg; Werner Stemer; Ralph Locher

(57) ABSTRACT

A method generates an image sequence using a tomosynthesis system. The image sequence represents an object under examination in rotating fashion. In a first step at least two projection data sets for the object under examination are captured. These have been acquired using different X-ray spectra in each case and from a plurality of acquisition angles in each case. In a further step at least one combination data set is calculated on the basis of the projection data sets. Subsequently in a further step the image sequence is calculated on the basis of the combination data set. An image sequence generating apparatus and a tomosynthesis system perform this described method.

13 Claims, 2 Drawing Sheets

(56) References Cited

U.S. PATENT DOCUMENTS

| | | | | |
|---|---|---|---|---|
| 2006/0002632 A1* | 1/2006 | Fu | ............................ | G06T 7/344 |
| | | | | 382/294 |
| 2006/0067473 A1* | 3/2006 | Eberhard | ................ | A61B 6/025 |
| | | | | 378/98.9 |
| 2006/0269040 A1* | 11/2006 | Mertelmeier | ........... | A61B 6/466 |
| | | | | 378/37 |
| 2007/0165922 A1* | 7/2007 | Webber | ..................... | A61B 6/12 |
| | | | | 382/128 |
| 2009/0147919 A1* | 6/2009 | Goto | ....................... | A61B 6/032 |
| | | | | 378/86 |
| 2010/0215233 A1* | 8/2010 | Hsieh | ...................... | A61B 6/032 |
| | | | | 382/131 |
| 2011/0158498 A1* | 6/2011 | Li | ........................... | G06T 11/008 |
| | | | | 382/132 |
| 2011/0188725 A1* | 8/2011 | Yu | .......................... | G06T 11/006 |
| | | | | 382/131 |
| 2012/0093278 A1* | 4/2012 | Tsukagoshi | ............ | G06T 11/008 |
| | | | | 378/4 |
| 2012/0134464 A1* | 5/2012 | Hoernig | ................. | A61B 6/025 |
| | | | | 378/22 |
| 2012/0189091 A1* | 7/2012 | Jerebko | ................. | A61B 6/5223 |
| | | | | 378/4 |
| 2012/0224668 A1* | 9/2012 | Baetz | .................... | A61B 6/4035 |
| | | | | 378/16 |
| 2012/0238870 A1* | 9/2012 | Smith | .................... | A61B 6/025 |
| | | | | 600/431 |
| 2012/0307965 A1* | 12/2012 | Bothorel | .................. | A61B 6/14 |
| | | | | 378/10 |
| 2013/0272494 A1* | 10/2013 | DeFreitas | .............. | A61B 6/025 |
| | | | | 378/37 |
| 2013/0329856 A1* | 12/2013 | Kuwahara | ............ | A61N 5/1039 |
| | | | | 378/62 |
| 2014/0050302 A1* | 2/2014 | Dennerlein | ........... | G06T 11/006 |
| | | | | 378/62 |
| 2014/0140604 A1* | 5/2014 | Carton | ................... | A61B 6/481 |
| | | | | 382/132 |
| 2014/0226783 A1* | 8/2014 | Ning | ...................... | A61B 6/032 |
| | | | | 378/5 |
| 2014/0376691 A1* | 12/2014 | Hoernig | ................. | G06T 11/006 |
| | | | | 378/37 |
| 2015/0154765 A1* | 6/2015 | Huo | ....................... | G06T 11/005 |
| | | | | 382/132 |
| 2016/0189376 A1* | 6/2016 | Bernard | ............... | G06T 11/006 |
| | | | | 382/132 |
| 2016/0256128 A1* | 9/2016 | Wang | ....................... | A61B 6/54 |
| 2017/0079607 A1* | 3/2017 | Claus | ....................... | A61B 6/5211 |
| 2017/0365076 A1* | 12/2017 | Ray | ....................... | G06T 11/008 |

\* cited by examiner

GENERATING AN IMAGE SEQUENCE

CROSS-REFERENCE TO RELATED APPLICATION

This application claims the priority, under 35 U.S.C. § 119, of German application DE 10 2016 211 766.1, filed Jun. 29, 2016; the prior application is herewith incorporated by reference in its entirety.

BACKGROUND OF THE INVENTION

Field of the Invention

The invention relates to a method for generating an image sequence, an image sequence generating apparatus and a tomosynthesis device.

Mammography continues to play an important role in the early detection of mammary carcinomas. In classic mammography, an X ray image of the female breast is created. To this end, X ray radiation having an energy spectrum which is dependent on the accelerating voltage is emitted by an X ray radiation source having a defined accelerating voltage. Accordingly the X ray energy is also simply denoted by the X ray voltage set (in kV). The X ray radiation used is normally a soft radiation having an energy of approximately 25 to 35 keV. The radiation penetrates an object under examination, is subsequently captured by a detector and converted into an electrical signal. The X ray images are viewed on a special mammography diagnostic station, by which they are represented visually.

In conventional two dimensional mammography, the problem exists that as a result of the overlapping of different tissue structures pathological changes in the tissue are frequently hidden, which means that they are not recognized. An attempt is made to compensate for this problem by recording the breast from two different angles, "craniocaudal" and "mediolateral oblique", in other words the one perpendicular and the other at a 45° angle thereto.

Compared with this, 3D breast tomosynthesis offers an imaging method in which the breast is recorded from many different angles. For example, projections are captured at angles of 15 to 50 degrees about the craniocaudal angular position, where the total dose corresponds approximately to that of a classic two dimensional mammogram. Images for individual slices of the breast tissue are normally calculated, in other words reconstructed, from the captured projection data. In order to reconstruct a volume data set for a region under examination from the captured projection data, the filtered back projection method is frequently employed. The resulting volume data set can be viewed slice by slice for diagnostic purposes. Since slices above and below the slice chosen for viewing in each case can be suppressed during the diagnosis, pathological changes in the tissue can as a general rule be more easily recognized. However, in this situation the slices are presented only from one direction, which means that depending on the location of the change in the tissue it can continue to prove difficult to detect and exactly localize said location.

It is furthermore known that it is possible to extrapolate back from the three-dimensional data set for tomosynthesis to a two dimensional image. A so-called synthetic two dimensional mammogram is generated by this means.

In order to allow the elimination of tissue structures which possibly mask lesions from the visual representation, in contrast enhanced dual energy mammography (CEDEM) after prior administration of contrast medium typically a high-energy recording is taken, followed by a low-energy mammography recording while maintaining the breast compression. Subsequently, following a registration and a weighted subtraction, a recombined result image is created in which essentially regions in which the contrast agent has been accumulated are represented in particularly well visible fashion. In other words, the different X ray energy levels are chosen such that the value of the lower energy lies below the energy value of the absorption edge of the contrast agent used for X ray radiation and the value of the higher energy lies above the energy value of the absorption edge of the contrast agent used for X ray radiation. Such a choice of the energy values of the X ray radiation for the different recordings means that the structures penetrated by the contrast agent in the breast tissue, such as lesions for example, are captured more clearly when imaging with X ray radiation having a higher energy level than when imaging with X ray radiation having a lower energy level. By generating a subtraction image from the two imaging processes, a representation of the lesions is obtained largely without background structures or tissue structures interfering with or obscuring the lesions, which facilitates detection of the lesions.

Furthermore, the contrast enhanced dual energy tomosynthesis (CEDET) method is also known, wherein a subtraction data set is calculated from a low-energy and a high-energy tomosynthesis data set, with the result that interfering structures can also be largely eliminated here in order to facilitate the detection of lesions.

SUMMARY OF THE INVENTION

An object of the present invention is to specify a method for generating an image sequence, an image sequence generating apparatus and a tomosynthesis system, and thereby to enable an improved representation of an object under examination.

The method according to the invention mentioned in the introduction for generating an image sequence by use of a tomosynthesis system, wherein the image sequence represents an object under examination in rotating fashion, includes the now described steps. In a first step, at least two projection data sets are firstly captured for the object under examination. The projection data sets have been acquired using different X ray spectra in each case and from a plurality of acquisition angles in each case. Subsequently in a second step, at least one combination data set is calculated on the basis of the projection data sets. In a third step, the image sequence is calculated on the basis of the combination data set.

The image sequence contains a plurality of individual images of the object under examination which are arranged in succession in a defined sequence or order. The image sequence represents the object under examination in rotating fashion, where the series of images reproduces views of the object under examination from a series of successive angular positions or perspectives to the object under examination as if an observer were for example to move in a circular path around the object under examination. The object under examination in question is preferably a body part or an organ of a patient, particularly preferably the breast of a female patient.

In this situation the projection data sets constitute raw data sets for the object under examination which have been acquired—preferably by a tomosynthesis device—from a multiplicity of different acquisition angles, in other words projection angles. In this situation the individual projection recordings are in each case, depending on the emitted X ray spectrum, in other words on the energy spectrum or on the wavelength range of the projected X ray radiation, assigned to a projection data set. In principle, more than two projection data sets having different spectra can be acquired. In order to minimize the exposure to radiation, projection data sets are preferably created for precisely two different X ray spectra. In this situation one of the X ray spectra typically exhibits a higher energy than the other. By particular preference, a high-energy projection data set and a low-energy projection data set are therefore acquired.

In the case of stored raw data sets, the capture of the raw data sets can take place by a transfer from a storage medium or by way of a computer network. Preferably however, the raw data sets are recorded by a tomosynthesis scan prior to execution of the method in a preparatory step not encompassed by the method according to the invention.

The at least two projection data sets are combined with one another either directly or indirectly, as will be explained in detail below. Combination in this situation basically means that corresponding data from the two data sets, in other words for example the brightness values and/or color values of corresponding image points, are computed together such that an enhanced contrast preferably results in image regions of interest from the combination of the high-energy projection data set and the low-energy projection data set. The combination data set is subsequently generated from the resulting values. Regions of interest in this situation are in particular those regions of the object under examination in which a pathological change in the tissue is suspected. It is thus possible for example to define a mixing ratio between the data sets for the resulting combination data set in a simple fashion. The combination can however also comprise further image processing steps such as for example logarithmization of the intensities, registration of the projection data sets with one another or the like.

The combination data set contains image data from which the image sequence is subsequently calculated. It is not however necessary to use the entire combination data set in order to calculate the image sequence. It is also possible to calculate images from the image data of the combination data set to form the image sequence only for selected angular positions, for example only every second acquisition angle, or only angular positions from a central region. According to the invention, the image sequence now exists in a format which can be evaluated by a human observer and can be displayed such that it creates the impression for the observer as if the object under examination represented were rotating. The image sequence in question obtained using the method according to the invention is in particular a so called rotating mammogram, in other words a rotating representation of a breast of a female patient.

In contrast to the prior art, the image sequence in question displayed according to the invention is therefore not a contrast-enhanced representation of individual images or of slice images of the object under examination but a preferably contrast-enhanced and rotating representation of the object under examination. This mode of representation enables a more accurate diagnosis of structures of interest which would otherwise extend perpendicular to the image plane or slice plane. Regions within the object under examination represented in rotating and preferably contrast-enhanced fashion in which a pathological change in the tissue is suspected can thereby be captured from different angles quasi three-dimensionally—for example as in a video film or as a video sequence—and thus better evaluated by an observer.

In order to generate an image sequence which represents an object under examination in rotating fashion, the image sequence generating apparatus mentioned in the introduction contains a capture unit and a calculation unit. The capture unit is configured such that it captures at least two projection data sets for an object under examination. The projection data sets have been acquired by using different X ray spectra in each case and from a plurality of acquisition angles in each case. The calculation unit is configured such that it calculates at least one combination data set on the basis of the projection data sets and calculates the image sequence on the basis thereof.

The tomosynthesis system mentioned in the introduction contains a tomosynthesis device and an image sequence generating apparatus according to the invention. The image sequence generating apparatus can for example be arranged in a user terminal additionally encompassed by the tomosynthesis system and be connected to the tomosynthesis device. Acquired data can thereby advantageously be represented directly according to the invention as an image sequence and appraised by medical staff.

The main components, in particular the calculation unit, of the image sequence generating apparatus according to the invention can be configured for the most part in the form of software components. In principle, the components can however also be implemented partly in the form of software-supported hardware, for example FPGAs or the like, in particular if the calculations in question are particularly fast. Likewise, the required interfaces can—for example if it is only a question of a transfer of data from other software components—be designed as software interfaces. They can however also be configured as interfaces built on a hardware basis which are driven by suitable software.

In particular, the image sequence generating apparatus according to the invention can be part of a user terminal or of a computer system of a tomosynthesis system.

A largely software-based implementation has the advantage that computer systems which have already been used previously can also be upgraded in a simple manner by a software update in order to operate in the inventive manner. In this regard the object is also achieved by a corresponding computer program product having a computer program which can be loaded directly into a storage device of an image sequence generating apparatus of a tomosynthesis system, having program sections in order to perform all the steps of the method according to the invention when the program is executed in the image sequence generating apparatus. In addition to the computer program, such a computer program product can where applicable include additional elements such as for example documentation and/or additional components, also hardware components such as for example hardware keys (dongles etc.) for using the software.

A computer-readable medium, for example a memory stick, a hard disk or some other transportable or fixedly installed data medium on which the program sections of the computer program which can be read in and executed by a computer unit of the image sequence generating apparatus are stored can be used for transportation to the image sequence generating apparatus and/or for storage on or in the image sequence generating apparatus. To this end, the computer unit can for example have one or more interoperating microprocessors or the like.

Further particularly advantageous embodiments and developments of the invention will emerge from the dependent claims and from the description below, where the independent claims of one claim category can also be developed in analogous fashion to the dependent claims of another claim category and in particular individual features of different exemplary embodiments or variants can also be combined to form new exemplary embodiments or variants.

With regard to a first variant of the method according to the invention, the combination data set is calculated directly from at least one part of the projection data sets. This is based on the prerequisite that one projection recording with a corresponding acquisition angle is present for each angular position to be calculated per projection data set. In other words, in the part of the projection data sets used having different X ray spectra, angle equality must prevail in each case between the corresponding projection recordings. At least two projection recordings having different X ray spectra or X ray energies, which are assigned in each case to a projection data set, are therefore preferably acquired for each angular position.

Given angle equality, the individual projection recordings can be merged directly, for example as a linear combination, in other words weighted pixelwise in additive or subtractive fashion, or can be combined using other common means of image processing, in other words for example displayed in false colors or the like. "Pixelwise" here means image point by image point. By means of this variant of the method according to the invention it is possible to generate an image sequence in a relatively simple manner which represents the object under examination in rotating and preferably contrast-enhanced fashion.

With regard to a second variant of the method according to the invention, an auxiliary image data set is reconstructed in each case from the projection data sets. The auxiliary image data sets are subsequently combined to form an auxiliary combination data set, on the basis of which the combination data set is calculated.

In this situation the auxiliary image data sets are a reconstructed 3D volume, reconstructed for example by means of filtered back projection. In other words, the two reconstructed volumes are where applicable registered with one another and combined preferably voxelwise, in other words volume image point by volume image point, in three dimensions to form the auxiliary combination data set, for example in analogous fashion to that described above in two dimensions. Projections are now preferably again generated from the combined three-dimensional volume by means of forward projection from defined directions or angular positions. In this situation the angular positions do not need to be identical to the original acquisition angles but can be chosen as required. With regard to a breast as the object under examination, the projections thus generated are also referred to as synthetic mammograms. With this variant, they form the combination data set. The image sequence is calculated as described above from said combination data set. The image sequence thus in particular represents a rotating synthetic mammogram of the object under examination.

With regard to a third variant of the method according to the invention, a first combination data set is generated in accordance with the second variant of the method according to the invention. In addition a second combination data set is generated in accordance with the first variant of the method according to the invention. Subsequently the first combination data set and the second combination data set are combined to form a third combination data set. The calculation of the image sequence takes place on the basis of the third combination data set.

Even if it is possible in principle for the first combination data set and the second combination data set to be based on different projection data sets, they are preferably generated on the basis of the same projection data sets. The generation of the first combination data set and of the second combination data set are temporally independent of one another in this situation, in other words the first combination data set can be created before, after or in parallel with the second combination data set.

The third combination data set is obtained from the first combination data set and the second combination data set for example by a simple linear combination, as already described above in analogous fashion for the combination of projection data sets. Furthermore, further common methods of image analysis and image processing can however in principle also be employed for example in order to particularly emphasize certain regions having well represented structures from the first combination data set or the second combination data set. With this variant, advantages of the first two variants can thus be utilized and at the same time their disadvantages can be avoided by way of a suitable combination of the two combination data sets.

With regard to a method according to the invention, at least one of the projection data sets is preferably recorded after administration of a contrast agent. Depending on requirements, one or more suitable substances can be employed as a contrast agent, for example iodine and/or gadolinium.

As already described further above, a low-energy projection data set and a high-energy projection data set are preferably captured as projection data sets.

In order to achieve a good contrast, it is basically sufficient if simply at least one projection data set having a higher-energy spectrum is recorded after the administration of contrast agent since the structures of interest thus already have contrast in comparison with the tissue background. The acquisitions of all the projection data sets do however preferably take place after the administration of contrast agent on account of any repositioning, which must be avoided, of the object under examination in the event of administration of contrast agent between acquisitions of individual projection data sets. An absorption edge of the contrast agent therefore preferably lies outside the X ray spectrum of at least one projection data set, whereas it lies in the X ray spectrum of at least one other projection data set. This is advantageous in particular in order to achieve a best possible contrast when all the projection data sets are acquired after administration of the contrast agent.

The calculation of the combination data set preferably takes place with the aid of a weighted subtraction. By particular preference a weighted subtraction of a low-energy data set from a high-energy data set is performed. With the first variant, the data sets are a low-energy projection data set and a high-energy projection data set respectively and with the second variant a low-energy auxiliary data set and a high-energy auxiliary data set respectively, which have been reconstructed from corresponding projection data sets.

The weighting takes place in this situation in such a manner that all those regions not of interest, in other words the tissue background, are attenuated as far as possible and the structures of interest are emphasized. In particular, when contrast agent is administered simultaneously pathological changes in the tissue can thus advantageously be enhanced and clearly represented.

The image sequence is preferably generated for a slice image subregion. In this situation the slice image subregion is a volume region of interest, a so-called "region of interest" (ROI), in which a change in the tissue is suspected. By restricting the method to the region defined in advance—for example through selection by an operator—it is advantageously possible to economize on computing power or to accelerate the calculation.

By preference the image sequence is displayed on a user terminal. The calculated image sequence is used for the assessment of structures of interest by an observer, in other words for example for the appraisal of a lump in a breast of a female patient by medical staff. This is made possible by the display according to the invention. In this situation the user terminal is preferably included in the tomosynthesis system, which means that an assessment can take place directly after the acquisition of the projection data sets. It is therefore possible to decide immediately whether the recorded data is sufficient or whether further data, for example in the context of an additional tomosynthesis scan, needs to be acquired. In the context of the invention, data acquired while the breast remains fixed can also be combined with the data sets already recorded previously.

The invention will be described again in detail in the following with reference to the attached figures on the basis of exemplary embodiments, where the same components are identified by the same reference characters in the different figures. The figures are as a general rule not to scale.

Other features which are considered as characteristic for the invention are set forth in the appended claims.

Although the invention is illustrated and described herein as embodied in a generating an image sequence, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 4:
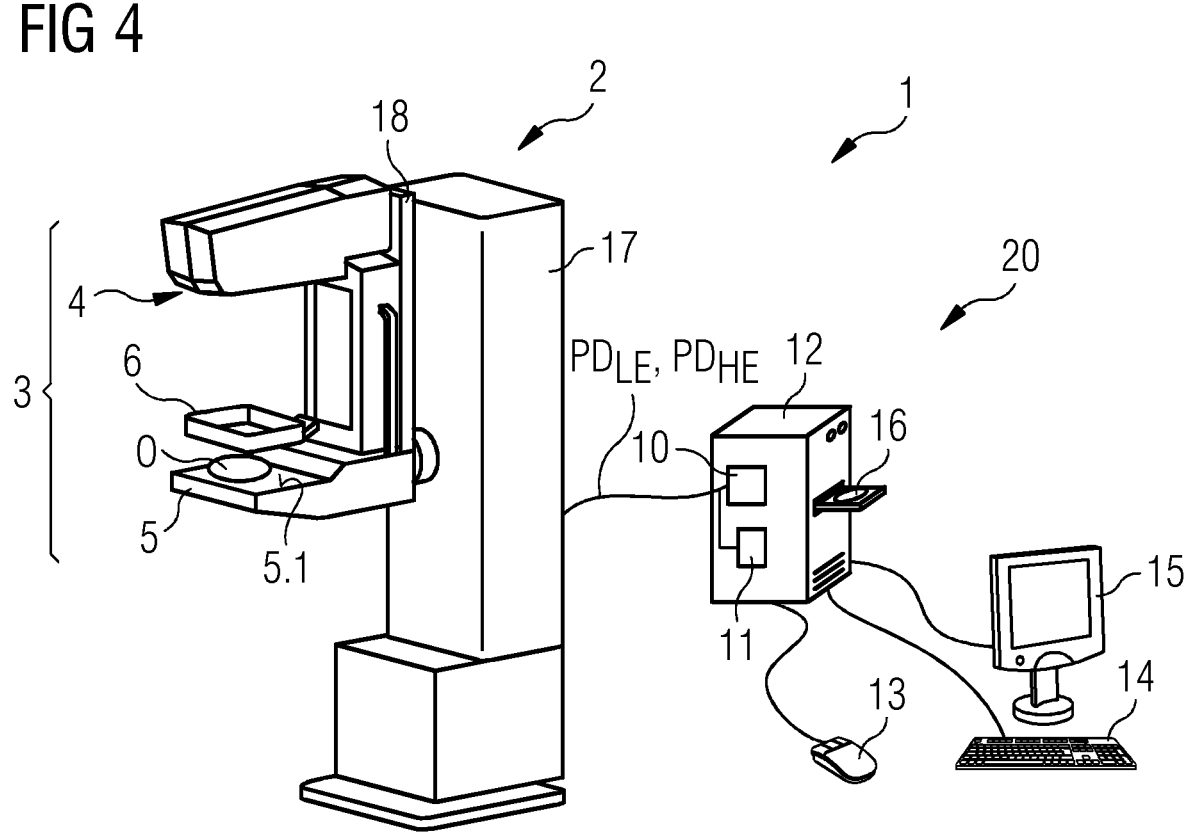
FIG. 4 is a diagrammatic, perspective view of an exemplary embodiment of a tomosynthesis system according to the invention.

Referring now to the figures of the drawings in detail and first, particularly to FIG. 4 thereof, there is shown a tomosynthesis system 1 according to the invention by way of example and in basic schematic form. Relative directional information such as "top", "and" etc. relate to a tomosynthesis system 1 set up as intended for operation. The tomosynthesis system 1 contains a tomosynthesis device 2 and a computer system 20. The tomosynthesis device 2 has a support column 17 and a source-detector arrangement 3, which in turn comprise an X ray radiation source 4 and a detector 5 having a detection surface 5.1. The support column 17 stands on the floor when operating. The source-detector arrangement 3 is connected thereto in adjustable fashion such that the height of the detector surface 5.1, in other words the distance to the floor, can be set to a breast height of a female patient.

As the object under examination O, a breast O of the female patient (illustrated here schematically) rests on the upper side of the detector surface 5.1 for an examination. Above the breast O and the detector surface 5.1 is arranged a plate 6 which is connected in adjustable fashion to the source-detector arrangement 3. For the examination the breast O is compressed and simultaneously fixed by lowering the plate 6 onto it such that a pressure is exerted on the breast O between plate 6 and detector surface 5.1.

The X ray radiation source 4 is arranged such opposite the detector 5 and configured such that the detector 5 captures X ray radiation emitted by the X ray radiation source 4 after at least part of the X ray radiation has penetrated the breast O of the female patient. Projections of the breast O are therefore captured as projection data in projection data sets PDLE, PDHE. In this situation the X ray radiation source 4 is pivotable relative to the detector 5 by a pivoting arm 18 in a range of ±50° about a home position, in which it stands perpendicular above the detection surface 5.1.

The computer system 20 contains an image sequence generating apparatus 12 and connected thereto in each case a mouse 13, a keyboard 14 and a screen 15. The screen 15 here serves as a display unit 15, the mouse 13 and the keyboard 14 each serve as an input device. The image sequence generating apparatus 12 contains a capture unit 10 and a calculation unit 11 (illustrated here schematically as blocks) and also a drive 16 for reading in from CD or DVD. In this situation the capture unit 10 and the calculation unit 11 can jointly use components of the image sequence generating apparatus 12, such as for example memory, processors and the like. The computer system 20 can be arranged in the same space as the tomosynthesis device 2 but it can also be situated in an adjacent control room or in a more distant space.

Figure 1:
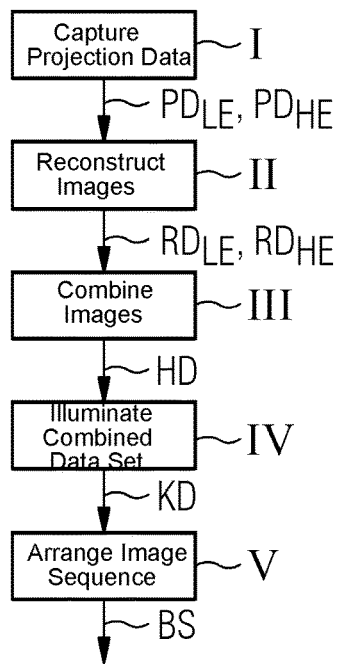
FIG. 1 is a schematic block diagram of a first exemplary embodiment of a method according to the invention for generating an image sequence.

A first exemplary embodiment of a method according to the invention for generating an image sequence is illustrated by way of example and schematically as a block diagram in FIG. 1. In a first step I, projection data PDLE, PDHE is captured by the capture unit 10 of the image sequence generating apparatus 12 by being transferred into the memory thereof and being stored there. The projection data PDLE, PDHE can have been acquired in a preparatory step, not included in the actual method, using a tomosynthesis system 1 (see FIG. 4) with iodine administered as a contrast agent. The projection data PDLE, PDHE can however for example also be retrievable in a suitable form from a storage device over a network or from a storage medium.

In this situation the projection data sets PDLE, PDHE comprise a low-energy projection data set PDLE and a high-energy projection data set PDHE. Both projection data sets PDLE, PDHE contain a number of projection recordings which have been acquired from different angles. The low-energy projection data set PDLE has been acquired using an X ray spectrum which lies beneath a K-absorption edge of the contrast agent iodine, also referred to for short in the following as X ray edge, at 33.17 keV. The high-energy projection data set PDHE exhibits at least a spectral range which lies above the X ray edge. This radiation will be absorbed more strongly in those regions of structures of interest of the breast O of the female patient in which the iodine has accumulated than elsewhere.

In a second step II, a low-energy auxiliary image data set RDLE is reconstructed from the low-energy projection data set PDLE and a high-energy auxiliary image data set RDHE is reconstructed from the high-energy projection data set PDHE. The common filtered back projection method is used in each case for the reconstruction. Both auxiliary image data sets RDLE, RDHE are thus reconstructed 3D volume data sets.

In a third step III, the auxiliary image data sets RDLE, RDHE are combined by means of a weighted subtraction to produce an auxiliary combination data set HD. On account of the possible deviations in reconstruction results it may firstly be necessary for that purpose to register the two auxiliary image data sets RDLE, RDHE with one another. This serves to ensure that corresponding volume image points, in other words voxels, of both auxiliary image data sets RDLE, RDHE are also situated at the same positions in the 3D volume of both auxiliary image data sets RDLE, RDHE. The low-energy auxiliary image data set RDLE is subsequently subtracted voxelwise, in other words voxel by voxel, from the high-energy auxiliary image data set RDHE. The subtraction takes place weighted with a factor so that background tissue outside the structures of interest is represented attenuated or at only negligible intensity. The impairment caused by the background tissue interfering with observation is thereby minimized, with the result that the structures of interest are emphasized.

In a fourth step IV, the auxiliary combination data set HD is projected virtually forward from defined angular positions, in other words quasi illuminated with different simulated angular settings by a virtual X ray radiation source. In this situation virtual projection recordings, so called synthetic mammograms, are generated. The synthetic mammograms form the combination data set KD.

In a fifth step V, the combination data set KD is arranged as an image sequence BS with successive angular positions of the individual synthetic mammograms. An incremental angular change of the breast O of the female patient thereby results between individual images of the image sequence BS. In this manner the images of the image sequence BS thus ordered in succession represent the breast O in rotating fashion—as for example in a video.

The steps II to V are performed by the calculation unit 11 of the image sequence generating apparatus 12 configured for the purpose.

Figure 2:
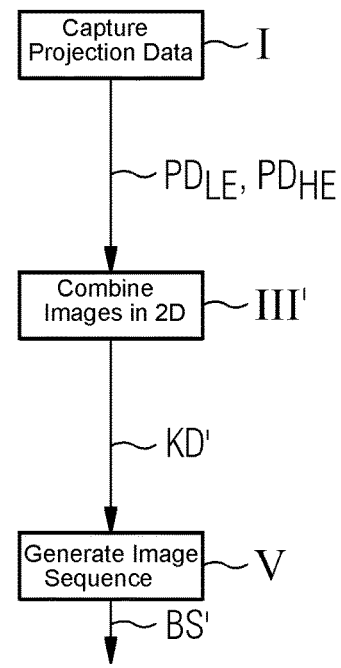
FIG. 2 is a schematic block diagram of a second exemplary embodiment of a method according to the invention for generating an image sequence.

FIG. 2 shows a schematic block diagram of a second exemplary embodiment of a method according to the invention wherein the steps I and III are essentially similar to the exemplary embodiment illustrated in FIG. 1. Prior to step I, during the acquisition at least one part of the projection recordings has been captured from the same acquisition angle for both projection data sets PDLE, PDHE.

This part of the projection data sets PDLE, PDHE is utilized in a following step III' for the combination. The projection recordings captured at the same angular position can be combined directly with one another. The combination takes place here in two dimensions—essentially in analogous fashion to the combination described with reference to FIG. 1—as a pixelwise weighted subtraction of the low-energy projection data set PDLE from the high-energy projection data set PDHE. "Pixelwise" means image point by image point. Here too the weighting factor is chosen such that background tissue outside the structures of interest is represented attenuated or at only negligible intensity and the structures of interest are emphasized.

The contrast-enhanced mammograms thus obtained form the combination data set KD'. From this, in step V, in analogous fashion to FIG. 1 an image sequence BS' is generated by the individual mammograms being ordered according to their angular positions and thus represent the breast O of the female patient in rotating fashion.

Figure 3:
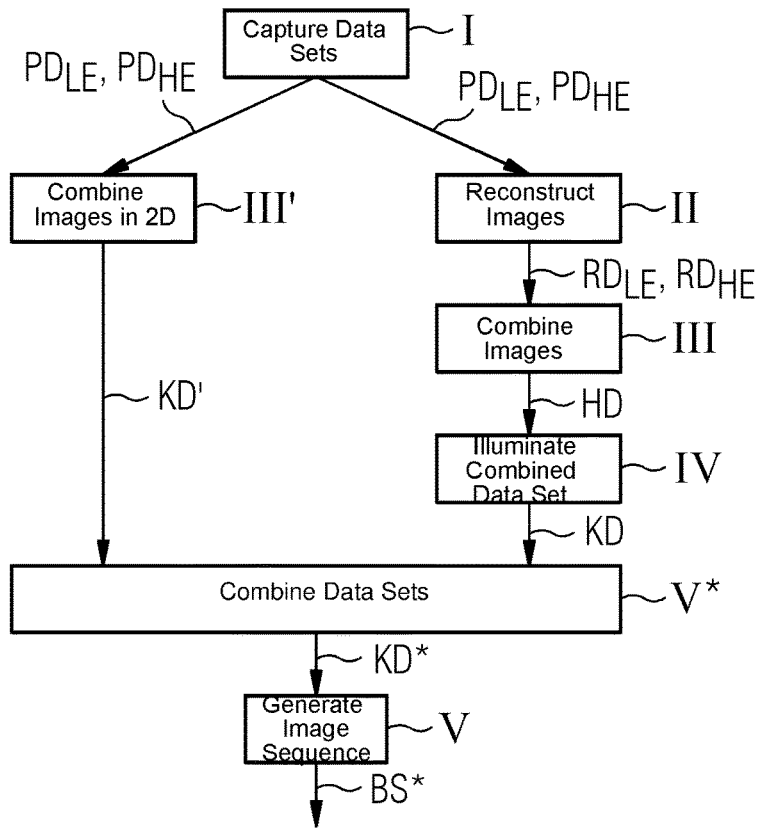
FIG. 3 is a schematic block diagram of a third exemplary embodiment of a method according to the invention for generating an image sequence.

FIG. 3 shows by way of example a schematic block diagram of a third method according to the invention for generating an image sequence BS. This exemplary embodiment combines the methods described with reference to FIG. 1 and FIG. 2 with one another. In step I, in analogous fashion to FIG. 2, the projection data sets PDLE, PDHE are captured. With the projection data sets PDLE, PDHE, now on the one hand the step III' is performed in analogous fashion to the description of FIG. 2 and on the other hand the steps II to IV are performed in analogous fashion to the description of FIG. 1. Depending on the computing power, this can happen in parallel or can also be processed in any desired sequence sequentially.

A first combination data set KD is obtained from step IV and a second combination data set KD' is obtained from step III'. These combination data sets KD, KD' are combined in an intermediate step V* to produce a third combination data set KD*. Where appropriate a registration of the two combination data sets KD, KD' with one another must firstly be performed for this purpose. The actual combination is performed as a linear combination, in other words the pixel values, thus for example a brightness value and/or RGB values, are weighted with a factor specified as required for the respective combination data set KD, KD' and then added pixelwise. In step V, as already described with reference to FIG. 1 and FIG. 2, the image sequence BS* is subsequently calculated from the combination data set KD*.

In a further exemplary embodiment, not illustrated here, of the method according to the invention an image sequence BS, BS', BS*, which has been created in accordance with the description of FIG. 1, FIG. 2 or FIG. 3, is represented on a user terminal of the tomosynthesis system 1. For this purpose the image sequence BS, BS', BS* is firstly converted where applicable into a suitable format and subsequently displayed on the screen 15. In this situation the display can take place as a forward running video. The image sequence BS, BS', BS* can however also be displayed running forward from the first image thereof to the last image and then running backward from the last image to the first image. Both types of display can also be reproduced quasi "continuously" in a loop. Furthermore, the display of the image sequence BS, BS', BS* can also be manipulated by an operator, the operator for example using the mouse 13 to scroll through the progression of the image sequence BS, BS', BS*.

Finally, it should be noted once again that devices and methods described in detail in the foregoing are only exemplary embodiments which can be modified in many different ways by the person skilled in the art without departing from the scope of the invention. It is thus also possible for example to administer a plurality of different contrast agents which accumulate in different tissue regions, which can thereby be emphasized more clearly in the combination data sets and finally in the image sequence. Furthermore, use of the indefinite article "a" or "an" does not mean that the features in question cannot also be present several times. Likewise the terms "unit" and "system" do not mean that the component in question cannot consist of a number of interacting subcomponents, which can in some instances also be spatially distributed.

The following is a summary list of reference numerals and the corresponding structure used in the above description of the invention:
1 Tomosynthesis system
2 Tomosynthesis device
3 Source-detector arrangement
4 X ray radiation source
5 Detector
5.1 Detection surface
6 Plate
8 Examination instrument, biopsy device
10 Capture unit
11 Calculation unit
12 Image sequence generating apparatus
13 Mouse
14 Keyboard
15 Display unit, screen
16 Drive
17 Support column
18 Pivoting arm
20 Computer system
O Object under examination, breast
PDLE Low-energy projection data set
PDHE High-energy projection data set
RDLE Low-energy auxiliary image data set
RDHE High-energy auxiliary image data set
HD Auxiliary combination data set
KD First combination data set
KD' Second combination data set
KD* Third combination data set
BS, BS', BS* Image sequence
I, II, III, III', IV, V, V* Method steps

The invention claimed is:

1. A method for generating an image sequence using a tomosynthesis system, which comprises the steps of:
    capturing at least two projection data sets for an object under examination, the two projection data sets being acquired using different X ray spectra in each case and from a plurality of acquisition angles in each case;
    calculating at least one combination data set on a basis of the projection data sets;
    calculating the image sequence, on a basis of the combination data set, for a slice image subregion being a volume region of interest in which a change in the tissue is suspected;
    arranging images of the image sequence in an order such that successively displaying the images of the image sequence in the order reproduces a rotating representation of the object under examination; and
    restricting the method to the volume region of interest in advance to thereby economize computing power or accelerate calculations.

2. The method according to claim 1, which further comprises calculating the combination data set directly from at least one part of the projection data sets.

3. The method according to claim 1, which further comprises:
    reconstructing an auxiliary image data set in each case from the projection data sets;
    combining the auxiliary image data sets to form an auxiliary combination data set; and
    calculating the combination data set on a basis of the auxiliary combination data set.

4. The method according to claim 1, which further comprises:
    reconstructing an auxiliary image data set in each case from the projection data sets;
    combining the auxiliary image data sets to form an auxiliary combination data set;
    calculating the combination data set being a first combination data set on a basis of the auxiliary combination data set;
    calculating a second combination data set directly from at least one part of the projection data sets;
    combining the first combination data set and the second combination data set to form a third combination data set; and
    performing a calculation of the image sequence on a basis of the third combination data set.

5. The method according to claim 1, which further comprises capturing at least one of the projection data sets after administration of a contrast agent.

6. The method according to claim 1, which further comprises performing a calculation of the combination data set with an aid of a weighted subtraction.

7. The method according to claim 1, which further comprises displaying the image sequence on a user terminal.

8. The method according to claim 1, which further comprises capturing a low-energy projection data set and a high-energy projection data set as the projection data sets.

9. The method according to claim 1, wherein the order is based on successive angular positions.

10. The method according to claim 1, which further comprises displaying the images of the image sequence in the order to display the rotating representation of the object under examination.

11. An image sequence generating apparatus, comprising:
    a computer configured for generating an image sequence representing an object under examination;
    said computer being configured to capture at least two projection data sets for the object under examination which have been acquired by using different X ray spectra in each case and from a plurality of acquisition angles in each case;
    said computer being configured to calculate at least one combination data set on a basis of the projection data sets, and said computer being configured to calculate the image sequence, on a basis of the combination data set, for a slice image subregion being a volume region of interest in which a change in the tissue is suspected, wherein the volume region of interest is defined in advance to thereby economize computing power or accelerate calculations;
    said computer being configured to arrange images of the image sequence in an order such that successively displaying the images of the image sequence in the order reproduces a rotating representation of the object under examination.

12. A tomosynthesis system, comprising:
a tomosynthesis device; and
a computer configured for generating an image sequence representing an object under examination;
    said computer being configured to capture at least two projection data sets for the object under examination which have been acquired by using different X ray spectra in each case and from a plurality of acquisition angles in each case;
    said computer being configured to calculate at least one combination data set on a basis of the projection data sets, and said computer being configured to calculate the image sequence on a basis of the combination data set, for a slice image subregion being a volume region of interest in which a change in the tissue is suspected, wherein the volume region of interest is defined in advance to thereby economize computing power or accelerate calculations; and said computer being configured to arrange images of the image sequence in an order such that successively displaying the images of the image sequence in the order reproduces a rotating representation of the object under examination.

13. A non-transitory computer-readable medium having computer-executable instructions to be executed on a computer for performing a method for generating an image sequence by a tomosynthesis system, the image sequence representing an object under examination, the method comprises the steps of:

capturing at least two projection data sets for the object under examination, the two projection data sets being acquired using different X ray spectra in each case and from a plurality of acquisition angles in each case;

calculating at least one combination data set on a basis of the projection data sets for a slice image subregion being a volume region of interest in which a change in the tissue is suspected, wherein the volume region of interest is defined in advance to thereby economize computing power or accelerate calculations;

calculating the image sequence on a basis of the combination data set; and arranging images of the image sequence in an order such that successively displaying the images of the image sequence in the order reproduces a rotating representation of the object under examination.

* * * * *